United States Patent
Hoheisel

(10) Patent No.: US 6,562,566 B1
(45) Date of Patent: May 13, 2003

(54) METHOD OF SEQUENCING BY OLIGOMER HYBRIDIZATION

(75) Inventor: Jörg Hoheisel, Wiesloch (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/011,075

(22) PCT Filed: Jul. 25, 1996

(86) PCT No.: PCT/DE96/01386

§ 371 (c)(1),
(2), (4) Date: May 3, 2000

(87) PCT Pub. No.: WO97/05276

PCT Pub. Date: Feb. 13, 1997

(30) Foreign Application Priority Data

Jul. 25, 1995 (DE) .......................................... 195 27 155

(51) Int. Cl.[7] .......................... C12Q 1/68; C12N 11/16; C07H 21/04; C12M 1/36
(52) U.S. Cl. ........................ 435/6; 435/174; 435/287.2; 536/24.3; 536/25.3
(58) Field of Search ........................ 435/6, 174, 287.2; 536/24.3, 25.3

(56) References Cited

U.S. PATENT DOCUMENTS

| | | | |
|---|---|---|---|
| 4,876,187 A | * 10/1989 | Duck et al. ................... | 435/6 |
| 5,403,711 A | 4/1995 | Walder et al. ................. | 435/6 |
| 5,683,874 A | * 11/1997 | Kool .............................. | 435/6 |
| 5,770,365 A | * 6/1998 | Lane et al. .................... | 435/6 |
| 5,800,992 A | * 9/1998 | Fodor et al. ................... | 435/6 |

FOREIGN PATENT DOCUMENTS

| | | |
|---|---|---|
| EP | A0 260 032 | 3/1988 |
| WO | WOA90/04652 | 5/1990 |

OTHER PUBLICATIONS

Hames et al. Nucleic Acid Hybridization: A practical approach. 1985. p. 81.*
Bains et al., 1988, "A Novel Method for Nucleic Acid Sequence Determination," *J. Theor. Biol.* 135:303–307.
Breslauer et al., 1986, "Predicting DNA Duplex Stability from the Base Sequence," *Proc. Natl. Acad. Sci. USA*, 83:3746–3750.
Drmanac et al., 1989, *Genomics* 4: 114–128.
Guo et al., 1994, "Direct Fluorescence Analysis of Genetic Polymorphisms by Hybridization with Oligonucleotide Arrays on Glass Supports," *Nucleic Acids Research* 22: 5456–5465.
Hoheisel, 1996, "Sequence–Independent and Linear Variation of Oligonucleotide DNA Binding Stabilities," *Nucleic Acids Research* 24: 430–432.

(List continued on next page.)

*Primary Examiner*—W. Gary Jones
*Assistant Examiner*—B J Forman
(74) *Attorney, Agent, or Firm*—Pennie & Edmonds LLP

(57) ABSTRACT

The present invention relates to a method of sequencing DNA by oligomer hybridization, DNA/RNA hybrid oligomers applied onto a support and optionally DNA oligomers and/or RNA oligomers being used as hybridization matrix.

7 Claims, 2 Drawing Sheets

OTHER PUBLICATIONS

Hoheisel et al., 1990, "Effect of 5–Bromo–and 5–Methyldeoxycyctosine on Duplex Stability and Discrimination of the NotI Octadeoxynucleotide," *J. Biol. Chem.* 265: 16656–56660.

Khrapko et al., 1991, *DNA Sequence 1*:375–388.

Matson et al., 1995, "Biopolymer Synthesis on Polypropylene Supports: Oligonucleotide Arrays," *Analytical Biochemistry 224:* 110–116.

Pease et al., 1994, "Light–Generated Oligonculeotide Arrays for Rapid DNA Sequence Analysis,"0 *Proc. Natl. Acad. Sci. USA 91:* 5022–5026.

Salazar et al., 1993, "The DNA Strand in DNA/RNA Hybrid Duplexes in Neither B–form nor A–form in Solution," *Biochemistry 32:* 4207–4215.

Sanghani and Lavery, 1994, "Theoretical Studies of DNA–RNA Hybrid Conformations," *Nucleic Acids Research 22:*1444–1449.

Southern et al., 1992, "Analyzing and Comparing Nucleic Acid Sequences by Hybridization to Arrays of Oligonucleotides: Evaluation Using Experimental Models," *Genomics 13:*1008–1017.

Stryer, 1988, "Biochemistry," *Freeman and Company, NY,* pp. 649–655.

Wood et al., 1985, *Proc. Natl. Acad. Sci. USA 82:*1585–1588.

* cited by examiner

FIG. 3  Plotting of the dissociation temperatures of the oligomers of the SX series as a function of the number of cycles between DNA and RNA nucleotides.

SEQUENCE LISTING

<160> NUMBER OF SEQ ID NOS: 13

<210> SEQ ID NO 1
<211> LENGTH: 13
<212> TYPE: DNA
<213> ORGANISM: Artificial Sequence
<220> FEATURE:
<223> OTHER INFORMATION: Synthesized oligomer

<400> SEQUENCE: 1
agtcccttgg ctc                                                          13

<210> SEQ ID NO 2
<211> LENGTH: 13
<212> TYPE: DNA
<213> ORGANISM: Artificial Sequence
<220> FEATURE:
<223> OTHER INFORMATION: Synthesized oligomer

<400> SEQUENCE: 2
gagccaaggg act                                                          13

<210> SEQ ID NO 3
<211> LENGTH: 12
<212> TYPE: DNA
<213> ORGANISM: Artificial Sequence
<220> FEATURE:
<223> OTHER INFORMATION: Synthesized oligomer

<400> SEQUENCE: 3
tctagagtcg ac                                                           12

<210> SEQ ID NO 4
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 4,9
<223> OTHER INFORMATION: RNA Nucleotides

<400> SEQUENCE: 4
tctagagtcg ac                                                           12

<210> SEQ ID NO 5
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 2,4,7,9,11
<223> OTHER INFORMATION: RNA Nucleotides

<400> SEQUENCE: 5
tctagagtcg ac                                                           12

<210> SEQ ID NO 6
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 2,4,5,6,7,9,10,11,12

```
<223> OTHER INFORMATION: RNA Nucleotides

<400> SEQUENCE: 6
tctagagtcg ac                                                              12

<210> SEQ ID NO 7
<211> LENGTH: 12
<212> TYPE: RNA
<213> ORGANISM: Artificial Sequence
<220> FEATURE:
<223> OTHER INFORMATION: Synthetic oligomer

<400> SEQUENCE: 7
ucuagagucg ac                                                              12

<210> SEQ ID NO 8
<211> LENGTH: 12
<212> TYPE: DNA
<213> ORGANISM: Artificial Sequence
<220> FEATURE:
<223> OTHER INFORMATION: Synthetic oligomer

<400> SEQUENCE: 8
gtcgactcta ga                                                              12

<210> SEQ ID NO 9
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 3,10
<223> OTHER INFORMATION: RNA Nucleotides

<400> SEQUENCE: 9
gtcgactcta ga                                                              12

<210> SEQ ID NO 10
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 1,3,5,8,10
<223> OTHER INFORMATION: RNA Nucleotides

<400> SEQUENCE: 10
gtcgactcta ga                                                              12

<210> SEQ ID NO 11
<211> LENGTH: 12
<212> TYPE: DNA
<213> ORGANISM: Artificial Sequence
<220> FEATURE:
<223> OTHER INFORMATION: Synthetic oligomer
<221> NAME/KEY: misc_feature
<222> LOCATION: 1,3,4,5,6,8,10,11
<223> OTHER INFORMATION: RNA Nucleotides

<400> SEQUENCE: 11
gtcgactcta ga                                                              12

<210> SEQ ID NO 12
<211> LENGTH: 12
<212> TYPE: DNA
```

-continued

```
<213> ORGANISM: Artificial Sequence
<220> FEATURE:
<223> OTHER INFORMATION: Synthetic oligomer
<221> NAME/KEY: misc_feature
<222> LOCATION: 1,3,4,5,6,7,8,9,10,11
<223> OTHER INFORMATION: RNA Nucleotides

<400> SEQUENCE: 12
gtcgacucua ga                                                             12

<210> SEQ ID NO 13
<211> LENGTH: 12
<212> TYPE: RNA
<213> ORGANISM: Artificial Sequence
<220> FEATURE:
<223> OTHER INFORMATION: Synthetic oligomer

<400> SEQUENCE: 13
gucgacucua ga                                                             12
```

METHOD OF SEQUENCING BY OLIGOMER HYBRIDIZATION

This is a national phase filing of the Application No. PCT/DE96/01386, which was filed with the Patent Cooperation Treaty on Jul. 25, 1996, and is entitled to priority of the German Patent Application 195 27 155.6, filed Jul. 25, 1995.

FIELD OF THE INVENTION

The present invention relates to a new method of sequencing by oligomer hybridization, DNA/RNA hybrid oligomers applied onto a support and optionally DNA oligomers and/or RNA oligomers being used as hybridization matrix.

BACKGROUND OF THE INVENTION

In addition to the DNA sequencing known for a long time and effected by the application onto gels, a further method was developed some years ago, namely the sequencing by oligomer hybridization. See, e.g., Drmanac et al., 1989, *Genomics* 4:114–128; Bains et al., 1988, *J. Theor. Biol.* 135:303–307. For this sequencing method a complete set of short oligonucleotides and oligomers, respectively, e.g., a set of all conceivable 65.536 octamers, is bound in an ordered grid on a support material, so that the position of each individual oligonucleotide is known. A DNA fragment whose sequence shall be determined is hybridized on such a hybridization matrix and an "oligomer chip", respectively, under conditions which only permit a specific duplex formation. As a result, the DNA fragment only binds to the oligomers whose complementary sequence corresponds accurately to a portion, e.g., an octamer when an "octamer chip" is used, of its own sequence. By the detection of the binding position of the hybridized DNA fragment, all oligomer sequences present in the fragment are thus determined. On account of the overlap of adjacent oligomer sequences, the continuous sequence of the DNA fragment can be determined by suitable mathematical algorithms. This principle is shown by way of example in FIG. 1 for a DNA fragment having a length of 13 bases, whose sequence shall be determined by octamer hybridization sequencing.

A major problem occurring when this method is practiced consists in that as a function of their sequence, the oligomers have a differing bond strength, i.e., dissociation temperature, but have to bind specifically and in full length to the DNA fragment to be determined under a single set of experimental hybridization temperatures. However, when high stringency is employed, weakly binding oligomers do not bind to the DNA fragment even though their complementary sequence is included therein (false negatives). In the case of low stringency, however, partial regions of oligomers, e.g., only six or seven nucleotides of an octamer, having high bond strength also bind, so that false positives form. Because of the width of the stability differences both artifacts occur under most conditions. For utilizing this sequencing technique it is therefore necessary to bring the bond strength of all oligomers to a level, irrespective of their sequence. By now, this has been done by varying the oligomer concentration. Khrapko et al., 1991, DNA *Sequence* 1:375–388. However, this is accompanied by the drawback that great technical difficulties occur when the hybridization matrix is produced, since a specific concentration has to be adjusted additionally for every oligomer. A second approach serving for bringing the bond strength of all oligomers to a level is represented by the introduction of base derivatives which result in a change of the stability of the particular base pairing. In connection therewith it is disadvantageous that many differing derivatives have to be used and the specificity of the base pairing is changed by the introduction of the derivatives. A third solution for modulating the bond strength of the oligomers provides for the hybridization in tetraalkylammonium salts which reduce the stability differences existing between G:C and A:T base pairs. Wood et al., 1985, *Proc. Natl. Acad. Sci. USA* 82:1585–1588. However, this effect is insufficient for short oligomers. Moreover, the use of the highly molar salt solutions impedes the hybridization. Therefore, it was the object of the present invention to bring the bond strength of all oligomers to a level in a sequencing method by means of oligomer hybridization and simultaneously avoid the above described drawbacks.

SUMMARY OF THE INVENTION

The present invention relates to a method of sequencing DNA by oligomer hybridization, DNA/RNA hybrid oligomers applied onto a support and optionally DNA oligomers and/or RNA oligomers being used as hybridization matrix.

BRIEF DESCRIPTION OF THE DRAWINGS

FIG. 3 depicts the plotting of the dissociation temperatures of the oligomers of the SX series as a function of the number of cycles between DNA and RNA molecules.

DETAILED DESCRIPTION OF THE INVENTION

Figure 1:
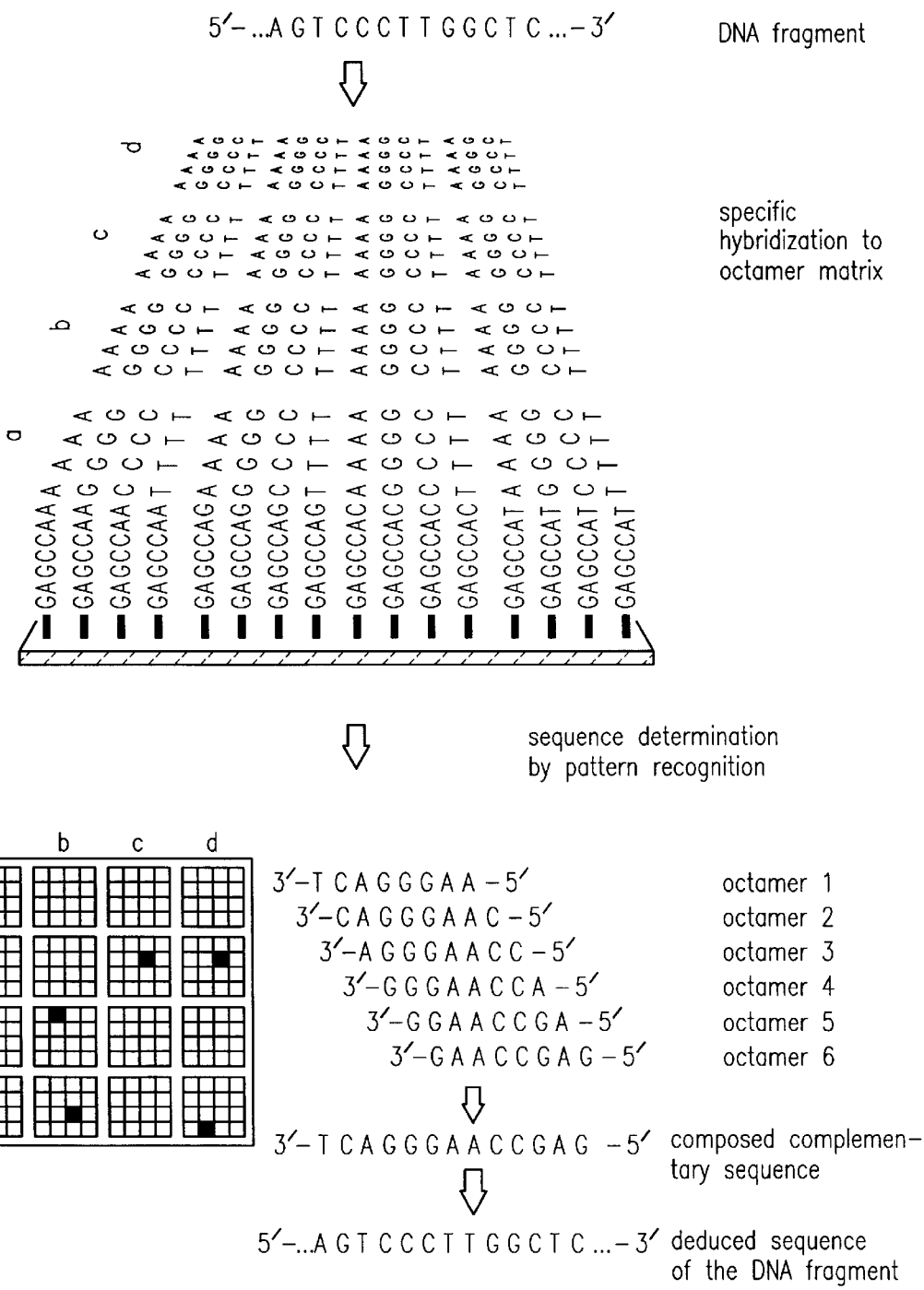
FIG. 1 depicts a principle of oligomer hybridization sequencing Seq. ID Nos. 1 and 2.

It is the object of the present invention to bring the bond strength of all oligomers to a level in a sequencing method by means of oligomer hybridization and simultaneously avoid the above described drawbacks.

This problem is solved by a method according to claim 1. Advantageous embodiments result from the subclaims.

The inventors found that by using DNA/RNA hybrid oligomers, optionally in combination with DNA and/or RNA oligomers,; on the hybridization matrix, the bond strength (duplex stability) can be varied when unknown DNA fragments are sequenced, by exerting an influence on the sugar folding or puckering without influencing the specificity of the base pairing. At the same time, the variation of the bond strength is independent of the base sequence of the oligomer because of the use of the DNA/RNA hybrids.

The DNA/RNA hybrid oligomers are synthesized by the common known methods which were developed for synthesizing pure DNA oligonucleotides, the necessary number of nucleotides only having to be doubled (DNA nucleotide and RNA nucleotide, respectively, of A, G, C and T). The synthesis is carried out preferably with the commercially available devices known on the market or slightly adapted devices. The application of the individual oligomers for the preparation of the hybridization matrix is made preferably via individual transfer of certain amounts to a certain position of a support by using a commercial robot. The person skilled in the art is familiar with materials for the support, with glass, polypropylene or silicon being preferably used. The oligomers are bound to the support surface preferably via commercially available linkers with which the person skilled in the art is familiar and which were optionally modified chemically as well.

However, there is also a possibility of simultaneously synthesizing all oligomers on the support. For this purpose, the synthesis building blocks are passed to four parallel channels, one in each case for the building blocks A, G, C, T with either deoxyribose or ribose sugar portion, via the support. In the second synthesis step, these channels are perpendicular as regards their orientation in the first step. In the third and fourth steps, four channels are used for the building blocks A, G, C, T for each individual channel of synthesis steps 1 and 2, so that a total of 16 channels are employed first in one dimension and then in the second dimension. For each further pair of synthesis steps, the number of channels is quadrupled each. This method is generally described in Southern et al., 1992, *Genomics* 13:1008–1017, to which reference is made herein.

A further method of simultaneously synthesizing all oligomers on the support was described by Pease et al., 1994, *Proc. Natl. Acad. Sci. USA* 91:5022–5026, to which reference is made herein. It synthesizes the oligonucleotides on the support by using building blocks which can be photoactivated and photolithographic techniques. The support is covered by a mask and irradiated with light. The surface is activated by the incidence of light only at those positions at which the mask has holes. A DNA or RNA nucleotide can be incorporated only at this activated position in the subsequent synthesis step. For the following synthesis step, a new mask is applied which has holes at another position, the surface of this new position is activated by light and a new DNA or RNA nucleotide is incorporated.

In practice, it has proved its worth to use a hybridization matrix onto which the octamers were applied ("octamer chip") for sequencing DNA fragments up to 200 bases, while DNA of 200 bases up to a kilobase in length are better sequenced by using a "decamer chip." The selection of a suitable oligomer size devolves on the skill of a person skilled in the art and comprises preferably a tetramer to dodecamer hybridization matrix.

The following experiments carried out with two different dodecamer sequences formed the basis of the present invention, capital letters representing DNA nucleotides and small letters RNA nucleotides. The following oligomers were prepared:

```
XS-0      TCTAGAGTCGAC  (SEQ ID NO:  3)
XS-17     TCTaGAGTcGAC  (SEQ ID NO:  4)
XS-42     TcTaGAgTcGaC  (SEQ ID NO:  5)
XS-67     TcTagagTcgac  (SEQ ID NO:  6)
XS-100    tctagagtcgac  (SEQ ID NO:  7)
SX-0      GTCGACTCTAGA  (SEQ ID NO:  8)
SX-17     GTcGACTCTaGA  (SEQ ID NO:  9)
SX-42     gTcGaCTcTaGA  (SEQ ID NO: 10)
SX-58     gTcgacTcTagA  (SEQ ID NO: 11)
SX-83     gTcgactctagA  (SEQ ID NO: 12)
SX-100    gtcgactctaga  (SEQ ID NO: 13)
```

Equal amounts of radioactively labeled oligomer were mixed each with single-stranded DNA which contains the complementary sequence. Non-specific binding did not take place. The single-stranded DNA oligomer mixture was applied to thin-film plates. Thin-film chromatography was carried out under hybridization conditions, a temperature gradient having been applied transversely to the flow direction. Under these conditions, free oligomer flows with the moving front of the buffer while bound oligomer stays at the starting point. A measurement of radioactivity at the starting point permits a quantification of the amount of bound oligomer. This measuring method was described in detail by Hoheisel et al., 1990, *J. Biol. Chem.* 165:16656–16660, to which reference is made herein.

Figure 2:
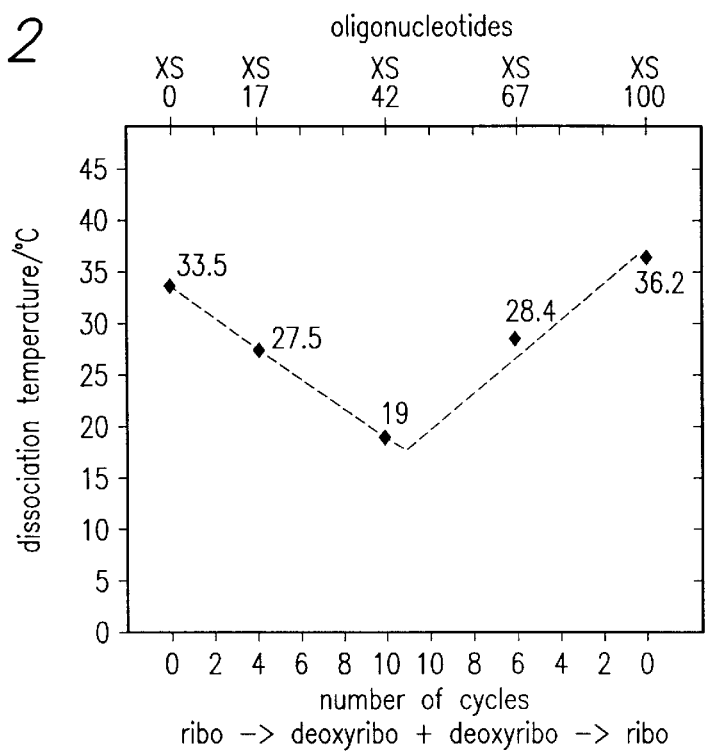
FIG. 2 depicts the plotting of the dissociation temperatures of the oligomers of the XS series as a function of the number of cycles between DNA and RNA molecules.
Figure 2:
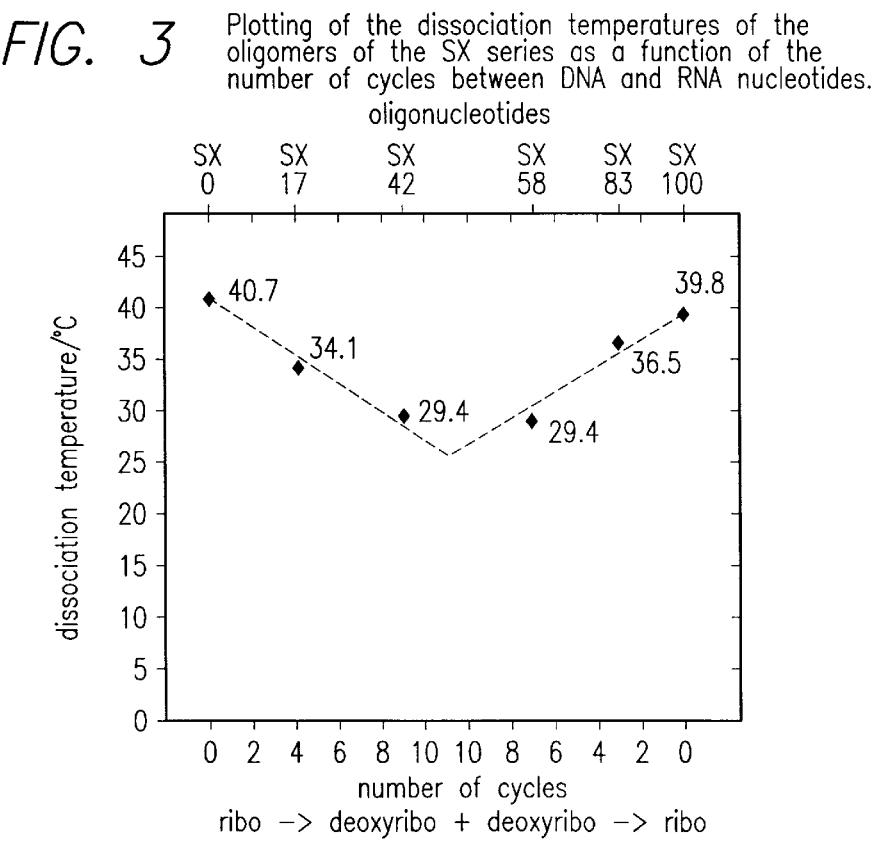

The dissociation temperature of the oligomers, among other, was also determined by the above experiment, i.e., the temperature at which 50% of the originally bound oligomer are still bound. It is evident from FIGS. 2 and 3 that with increasing number of cycles from DNA nucleotide to RNA nucleotide and from RNA nucleotide to DNA nucleotide, respectively, the duplex stability decreases linearly. Cycles are understood to mean the number of alterations between DNA and RNA in a molecule. Thus, 7 cycles take place in fragment "AgCtTgAg" and only 1 cycle in fragment "AGCTTgag."

In order to bring the bond strength of the oligomers on the hybridization matrix ("oligomer chip") to a level, the dissociation temperatures of pure DNA oligomers on a "test chip" have to be determined by means of hybridizations with a DNA test fragment of known sequence. Since it is known from the very beginning to which oligomers of the "test chip" the test fragment may bind and to which it may not bind (false positives), the dissociation temperature of the oligomers to which the fragment was allowed to bind and was bound, is determined. This procedure is repeated with further DNA test fragments until the dissociation temperatures of all oligomers of the chip have been determined. Then, the determined lowest dissociation temperature is assumed to be that to which all oligomers shall be adjusted to bring all oligomers to a level of bond strength. This is made by introducing RNA nucleotides into the corresponding oligomers when a new chip is synthesized, i.e., the corresponding DNA/RNA cycles are introduced and the dissociation temperature of the oligomer is lowered. It is preferred that the DNA/RNA hybrid oligomers have at least 2 cycles from DNA to RNA and from RNA to DNA, respectively, and at least 4 cycles are especially preferred. On this basis, a chip is obtained which distinguishes itself by a uniform bond strength of all oligomers and is suited for sequencing an unknown DNA fragment. It is also within the scope of this invention to apply RNA oligomers onto a "test chip" and test them so as to subsequently introduce DNA nucleotides for the preparation of the DNA/RNA hybrid oligomers.

Another, but not so precise, possibility of predicting the bond strength is a calculation method based on the base sequence. This method was described by Breslauer et al., 1986, *Proc. Natl. Acad. Sci. USA* 83:3746–3750, and can supply a quick survey when a computer is used.

All references cited in this application are hereby incorportated by reference in their entirety.

What is claimed:

1. A method of sequencing a DNA fragment by oligomer hybridization, comprising:

(a) providing a hybridization matrix comprising single-stranded oligomers composed of DNA and RNA nucleotides, wherein all single-stranded oligomers are adjusted to bring said oligomers to a uniform bond strength that is sequence-independent;

(b) exposing a DNA fragment of interest to said hybridization matrix;

(c) determining the positions on said hybridization matrix to which said DNA fragment hybridizes; and (d) deducing the sequence of said DNA fragment.

2. The method of claim 1, wherein said hybridization matrix further comprises DNA oligomers and/or RNA oligomers.

3. The method of claim 1 or 2, wherein said support is a material selected from the group consisting of glass, polypropylene and silicon.

4. The method of claim 1 or 2, wherein said oligomers of said hybridization matrix are oligonucleotide tetramers to oligonucleotide dodecamers.

5. The method of claim 1 or 2, wherein said hybridization matrix is generated by synthesizing said oligomers on the support using building blocks which can be photoactivated, using photolithographic techniques.

6. The method of claim 1 or 2, wherein said hybridization matrix is generated by:

(a) synthesizing said oligomers of said support individually; and (b) applying said oligomers on the support surface by means of a linker.

7. The method of claim 1 or 2, wherein said oligomers shift at least four times from DNA to RNA and from RNA to DNA.

* * * * *